United States Patent [19]

Todd et al.

[11] Patent Number: 5,378,617

[45] Date of Patent: * Jan. 3, 1995

[54] PROCESS FOR THE PRODUCTION OF MACROLIDE COMPOUNDS

[75] Inventors: Martin Todd, High Wycombe; Mark A. Haxell, St. Peters; Gordon C. Lawrence, Burnham, all of England

[73] Assignee: American Cyanamid Company, Wayne, N.J.

[*] Notice: The portion of the term of this patent subsequent to Feb. 6, 2007 has been disclaimed.

[21] Appl. No.: 933,578

[22] Filed: Aug. 24, 1992

Related U.S. Application Data

[63] Continuation of Ser. No. 492,250, Mar. 9, 1990, abandoned, which is a continuation of Ser. No. 24,664, Mar. 11, 1987, abandoned.

[30] Foreign Application Priority Data

Mar. 12, 1986 [GB] United Kingdom ............... 8606120

[51] Int. Cl.⁶ .................... C12P 17/18; C12N 1/20
[52] U.S. Cl. ................... 435/119; 435/253.5; 435/244; 435/76
[58] Field of Search ........ 435/119, 253.5, 886, 435/244, 76

[56] References Cited

U.S. PATENT DOCUMENTS 4,310,519  1/1982  Albers-Schonberg ............... 435/76

FOREIGN PATENT DOCUMENTS 1390336  4/1975  United Kingdom ...... C07D 493/29

OTHER PUBLICATIONS

Gullo et al., Abstr. Pap. Am Chem. Soc. 1983, (1986 Meet. MBTD28).
Stark et al., *Antimicrob. Agents and Chemotherapy*, 1967 pp. 353-358.

Primary Examiner—Irene Marx
Attorney, Agent, or Firm—Bacon & Thomas

[57] ABSTRACT

A process for the production of a compound of formula (I)

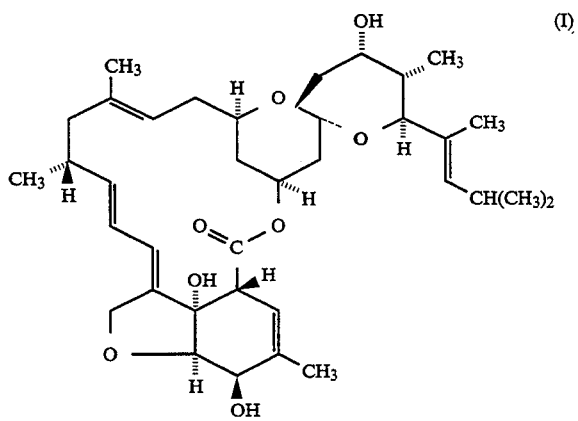

which comprises cultivating a microorganism of the genus *Streptomyces* capable of producing the compound of formula (I) in the presence of one or more fatty acids and/or salts, esters and amides of these acids, whereby the compound of formula (I) is produced, and if desired isolating the said compound. The fatty acid increases the yield of the formula (I) compound and is preferably isobutyric or valeric acid.

4 Claims, No Drawings

PROCESS FOR THE PRODUCTION OF MACROLIDE COMPOUNDS

This application is a continuation of application Ser. No. 07/492,250, filed Mar. 9, 1990 now abandoned; which is a continuation of 07/024,664, filed Mar. 11, 1987, now abandoned.

This invention relates to a new process for the production of an antibiotic compound. In particular it relates to a process for the production of an antibiotic compound by cultivation of Streptomyces microorganisms.

United Kingdom Patent Specification No. 2166436 and European Patent Specification No. 170006 describe the production of a class of compounds, which we have designated Antibiotics S541. Antibiotics S541 substances have antibiotic and, in particular, anti-endoparasitic, anti-ectoparasitic, anti-fungal, insecticidal, nematicidal and acaricidal activity and are of special interest for use in agriculture, horticulture, and animal and human health. Antibiotics S541 substances are also useful as intermediates in the preparation of other compounds having the antibiotic activity referred to above.

An Antibiotics S541 compound of special interest is the compound of formula (I)

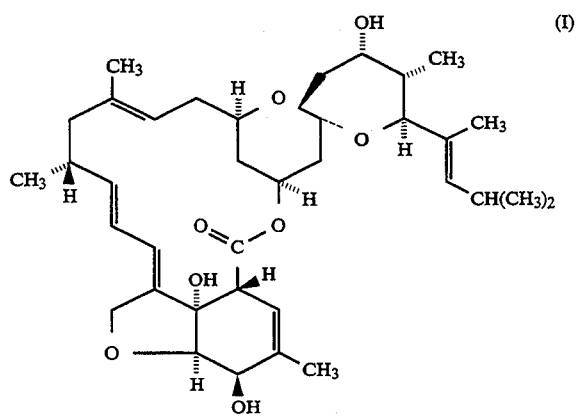

UK Patent Specification No 2166436 and European Patent Specification No 170006 describe the production of the compound of formula (I) and other Antibiotics S541 compounds by cultivation of microorganisms belonging to the genus Streptomyces. Under the normal cultivation conditions described in these patent applications the Streptomyces microorganisms produce a mixture of different Antibiotics S541 compounds. This gives rise to two problems when a particular Antibiotics S541 compound is required. Firstly, the titre of the desired Antibiotics S541 compound is reduced and, secondly, the isolation and separation of the desired compound is difficult from a mixture of related compounds.

We have now found that it is possible to cultivate an Antibiotics S541 producing Streptomyces strain in a manner such that the microorganism produces the compound of formula (I) above in a higher proportion relative to other Antibiotics S541 compounds than in the case when the microorganism is fermented under normal fermentation conditions. In general, the improvement is achieved by cultivating the Streptomyces microorganism in the presence of fatty acids and salts, esters and amides thereof. In this way, the titre of the compound of formula (I) is increased and the isolation and separation of the compound of formula (I) is made easier, and, advantageously, higher yields of the compound are thus obtained.

Thus, according to one aspect of the invention we provide a process for the production of a compound of formula (I) which comprises cultivating a microorganism of the genus Streptomyces capable of producing the compound of formula (I) in the presence of one or more fatty acids and/or salts, esters and amides of these acids, whereby the compound of formula (I) is produced, and if desired isolating the said compound.

Microorganisms capable of producing the compound of formula (I) may readily be identified using a convenient small scale test employing the nematode Caenorhabditis elegans, for example by adding a test sample [obtained from fermentation of the microorganism] to a suspension of the nematode and examining the consequent effect on nematode visability and by analytical high performance liquid chromatography on the test sample.

The microorganism will preferably be of the species Streptomyces thermoarchaensis, or Streptomyces cyaneogriseus noncyanogenus, in particular Streptomyces thermoarchaensis NCIB 12015 (deposited Sep. 10, 1984), Streptomyces thermoarchaensis NCIB 12111, 12112, 12113 and 12114 (all deposited Jun. 26, 1985) and Streptomyces cyaneogriseus noncyanogenus NRRL 15773 (deposited May 3, 1984) and mutants of all these strains.

All of the above-mentioned microorganisms which are identified with their accession numbers have been deposited in the permanent culture collection of the National Collections of Industrial and Marine Bacteria, Torry Research Station, Aberdeen, United Kingdom.

Streptomyces thermoarchaensis NCIB 12015 has the following taxonomic characteristics:

| CHARACTER | RESULT |
| --- | --- |
| Spore chain verticillati | − |
| Spore chain retinaculiaperti | − |
| Spore chain rectiflexibiles | − |
| Spore chain spirales | + |
| Fragmentation of mycelium | − |
| Spore surface smooth | + |
| Spore surface rugose | − |
| Spore color grey | + |
| Spore color red | − |
| Spore color green | − |
| Reverse yellow/brown | + |
| Reverse red/orange | − |
| Melanin production | − |
| Use of adonitol | − |
| Use of cellobiose | + |
| Use of D-fructose | + |
| Use of meso-inositol | − |
| Use of inulin | + |
| Use of mannitol | − |
| Use of raffinose | + |
| Use of rhamnose | + |
| Use of D-xylose | + |
| Use od DL-a-aminobutyric acid | − |
| Use of L-histidine | + |
| Use of L-hydroxyproline | − |
| Degradation of allantoin | + |
| Degradation of arbutin | + |
| Degradation of xanthine | + |
| Degradation of pectin | + |
| Degradation of lecithin | − |
| Nitrate reduction | + |
| Hydrogen sulphide production | + |
| Tolerance of sodium azide (0.01%, w/v) | − |
| Tolerance of sodium chloride (7%, w/v) | − |
| Tolerance of phenol (0.1%, w/v) | + |
| Growth at 45° C. | + |

-continued

| CHARACTER | RESULT |
| --- | --- |
| Resistance to neomycin (50 µg · ml$^{-1}$) | − |
| Resistance to rifampicin (50 µg · ml$^{-1}$) | + |
| Antibiosis to *Aspergillus niger* LIV 131 | + |
| Antibiosis to *Bacillus subtilis* NCIB 3610 | − |
| Antibiosis to *Streptomyces murinus* ISP 5091 | + |

Strains NCIB 12111, 12112, 12113 and 12114 all have substantially similar essential characteristics. However, NCIB 12111 requires adenine for growth, NCIB 12112 requires serine for growth, NCIB 12113 requires histidine for growth and NCIB 12114 is resistant to Streptomycin.

Mutants of the above strains may arise spontaneously or may be produced by a variety of methods including those outlined in Techniques for the Development of Micro-organisms by H. I. Adler in 'Radiation and Radioisotopes for Industrial Microorganisms', Proceedings of the Symposium, Vienna 1973, p241, International Atomic Energy Authority. Such methods include ionising radiation, chemical methods e.g. treatment with N-methyl-N'-nitro-N-nitrosoguanidine (NTG); heat; genetic techniques, such as recombination, transduction, transformation, lysogenisation and lysogenic conversion, and selective techniques for spontaneous mutants and mutants of all these strains.

Fatty acids which may be used according to the process of the present invention will include any fatty acids which provide the compound of formula (I) in a higher proportion relative to other Antibiotics S541 compounds than in the case when the fermentation is carried out under normal condition. Fatty acids capable of effecting an improvement in the proportion of the compound of formula (I) relative to other Antibiotics S541 compounds may readily be identified using a convenient small scale fermentation and examining the effect of adding different fatty acids by analytical high performance liquid chromatography of the test sample. Examples of fatty acids which may be used according to the process of the present invention include organic acids containing up to ten carbon atoms, eg three to eight carbon atoms.

Particularly suitable fatty acids include isobutyric acid and valeric acid.

Thus, in a preferred aspect of the present invention we provide a process for the preparation of a compound of formula (I) which comprises cultivating a microorganism of the genus *Streptomyces* capable of producing the compound of formula (I) in the presence of one or more compounds selected from isobutyric acid, valeric acid and the salts, esters, and amides of these acids, whereby the compound of formula (I) is produced, and if desired isolating the said compound.

Examples of suitable salts of the fatty acids include alkali metal salts such as potassium or sodium salts. Suitable esters include alkyl esters e.g. $C_{1-4}$ alkyl esters such as methyl or ethyl esters.

We have found it advantageous to carry out the process of the invention in the presence of two fatty acids or salts thereof. Use of both acids or their salts in the same fermentation produces the compound of formula (I) in a desirably high ratio relative to other Antibiotics S541 compounds. Thus, in a particularly preferred aspect of the invention we provide a process for the production of a compound of formula (I) which comprises cultivating a microorganism of the genus *Streptomyces* capable of producing the compound of formula (I) in the presence of two fatty acids or salts thereof, whereby the compound of formula (I) is produced, and if desired isolating said compound therefrom.

We have found that it is especially advantageous to carry out the process of the invention in the presence of isobutyric acid and valeric acid or salts thereof. Use of both acids or their salts in the same fermentation produces the compound of formula (I) in a desirably high ratio relative to other Antibiotics S541 compounds. Thus, in a particular aspect of the invention we provide a process for the production of a compound of formula (I) which comprises cultivating a microorganism of the genus *Streptomyces* capable of producing the compound of formula (I) in the presence of isobutyric acid or a salt thereof and valeric acid or a salt thereof, whereby the compound of formula (I) is produced, and if desired isolating said compound therefrom.

Where more than one fatty acid substance is added to the fermentation the fatty acid substances may be added together in a set ratio or, preferably, independently of each other. The ratio may be changed during the cultivation as desired either by keeping the quantity of one substance constant and changing the quantity of the other or by altering the quantities of both substances. The exact quantities will need to be empirically determined to meet the requirements of the cultivation. The culture medium used for cultivating the microorganism producing the compound of formula (I) is that which would normally be used for the production of the said compound, but with the fatty acid(s) or salts, esters or amides thereof added.

In general the fatty acid substance(s) may be added at any time during the cultivation of the microorganism. We have found it preferable however to begin adding the substance(s) when the pH of the culture medium begins to change away from the natural pH of around 5.5 to 7.5 and/or the microorganism begins to produce the compound of formula (I). This may generally happen at around 18 hours into the cultivation. At this point the fatty acid substance(s) is/are added to control the pH at the desired level (i.e. around pH 5.5 to 7.5, e.g. pH 7.2 to 7.4). The same or different fatty acid substance(s) may then be added throughout the zest of the fermentation to maintain the pH of the desired level. Alternatively, the fatty acid substance(s) may be added at a fixed rate throughout the rest of the fermentation with an aqueous acid (e.g. sulphuric acid) or a base (e.g. sodium hydroxide) added as appropriate to maintain the pH at the desired level. The quantity of fatty acid substance(s) required will vary over a wide range depending on the nature of the culture medium and *Streptomyces* strain used and generally needs to be empirically determined to meet the requirements of each cultivation. It is also important to determine empirically whether it is necessary to have an accumulation of the fatty acid substance(s) in the medium. However, we have found that it may be preferable to avoid adding the fatty acid substance(s) in a quantity which allows accumulation to take place when the fermentation is carried out using a microorganism of the species *Streptomyces thermoarchaensis* or *Streptomyces cyaneogriseus noncyanogenus*.

In the process according to the invention, the culture medium will in general contain other assimilable sources of carbon, nitrogen and mineral salts in addition to the fatty acid substance(s) discussed above. Suitable sources of carbon, nitrogen and mineral salts are discussed in UK Patent Specification No 2166436 and European Patent Specification No 170006.

Cultivation of the *Streptomyces* organism will generally be effected according to the methods described in UK Patent Specification No. 2166436 and, if desired, the compound of formula (I) may be separated from the whole fermentation by conventional isolation and separation techniques as described in the aforementioned UK and European Patent Specifications. UK Patent Specification No 2166436 and European Patent Specification No 170006 also describe suitable methods for purifying the compound of formula (I).

The following Example illustrates the invention. In the following examples L means litre.

EXAMPLE 1

Spores of *Streptomyces thermoarchaensis* NCIB 12015 were inoculated onto agar slants made up of the following ingredients:

|  | $gL^{-1}$ |
| --- | --- |
| Yeast extract (Oxoid L21) | 0.5 |
| Malt extract (Oxoid L39) | 30.0 |
| Mycological Peptone (Oxoid L40) | 5.0 |
| Agar No. 3 (Oxoid L13) | 15.0 |

Distilled water to 1 L, pH approximately 5.4.

and incubated at 28° C. for 10 days. The mature slant was then covered with a 20% glycerol solution (6 ml) and scraped with a sterile tool to loosen the spores and mycelium. 0.4 ml of the resulting spore suspension was used to inoculate a 250 ml Erlenmeyer flask containing Medium A:

| Medium A | $gL^{-1}$ |
| --- | --- |
| Glucose | 2.5 |
| Malt Dextrin MD 30E | 25.0 |
| Arkasoy 50 | 12.5 |
| Molasses | 1.5 |
| $K_2HPO_4$ | 0.125 |
| $CaCO_3$ | 1.25 |
| 3-(N-Morpholino) propane-sulphonic acid (MOPS) | 21.0 |

Distilled water to 1L, pH adjusted to pH 6.5 before autoclaving.

The culture was incubated at 28° C. for 2 days on a rotary shaker operated at 250 rpm with a 50 mm diameter orbital motion. 2% (v/v) portions of the 2 day developed inoculum were used to inoculate further 250 ml Erlenmeyer flasks containing Medium A (5 ml) and incubated as previously described.

80 ml of the bulked shake flask developed inoculum was used to inoculate a fermenter (7 L) containing Medium B (4 L):

| Medium B | $gL^{-1}$ |
| --- | --- |
| Glucose | 3.75 |
| Malt Dextrin MD 30E | 37.5 |
| Arkasoy 50 | 18.8 |
| Molasses | 2.25 |
| $K_2HPO_4$ | 0.188 |
| $CaCO_3$ | 1.88 | pH adjusted to pH 6.5 before autoclaving.

The fermentations were controlled to a temperature of 35° C. The culture was agitated at 500 rev/min and aerated at 3 L/min. The pH was controlled to prevent the pH rising above pH 7.2–7.4 either by addition of:

(i) 10% $H_2SO_4$ (according to the method described in Example 5 in UK Patent Specification No 2166436) 80 ml 10% $H_2SO_4$ used for pH control and harvested at 114 h.

(ii) 50/50 valeric acid/isobutyric acid 110 mls 50/50 valeric acid/isobutyric acid was used for pH control from 18–138 h i.e. an average of 2.75 g valeric acid was used/L/day Similarly an average of 2.75 g isobutyric acid was used/L/day.

(iii) 40/60 valeric acid/isobutyric acid 115 ml 40/60 valeric acid/isobutyric acid used for pH control from 18–138 h i.e. an average of 2.3 g valeric acid was used/L/day i.e. an average of 3.45 g isobutyric acid was used/L/day.

(iv) 30/70 valeric acid/isobutyric acid 125 ml 30/70 valeric acid/isobutyric acid used for pH control from 18–138 h ie an average of 1.875 g valeric acid was used/L/day ie an average of 4.375 g isobutyric acid was used/L/day (v) 60/40 valeric acid/isobutyric acid 115 ml 60/40 valeric acid/isobutyric acid used for pH control from 18–138 h ie an average of 3.45 g valeric acid was used/L/day ie an average of 2.3 g isobutyric acid was used/L/day The fermentations were harvested at 138 h unless otherwise stated and titres of the compound of formula (I) determined as follows:

| Acid for pH control | Compound of formula (I) mg/L | % Total Antibiotics S541 Compounds |
| --- | --- | --- |
| (i) $H_2SO_4$ = normal pH control | 284 | 46 |
| (ii) 50/50 valeric acid/ isobutyric acid | 474 | 55 |
| (iii) 40/60 valeric acid/ isobutyric acid | 504 | 64 |
| (iv) 30/70 valeric acid/ isobutyric acid | 236 | 78 |
| (v) 60/40 valeric acid/ isobutyric acid | 348 | 49 |

EXAMPLE 2

The fermentation of Example 1 was repeated but using Medium C (4 L) in place of Medium B.

| Medium C | $gL^{-1}$ |
| --- | --- |
| Meritose | 45.0 |
| Arkasoy 50 | 18.8 |
| Molasses | 2.2 |
| $K_2HPO_4$ | 0.18 |
| $CaCO_3$ | 1.8 |
| Silicone 1520 | 0.625 |

Distilled water to 1 L, pH adjusted to 6.5 with aqueous $H_2SO_4$ before autoclaving.

The fermentations were controlled to a temperature of 35°. The culture was agitated at 500 rev/min and aerated at 3 L/min. The fermentations were also subjected to the following conditions:

(i) 10% $H_2SO_4$ added to prevent the pH rising above pH 7.2–7.4. 100 ml 10% $H_2SO_4$ used for pH control. The fermentation was harvested at 138 h.

(ii) Isobutyric acid added at an average rate of 2.63 g/L/day from 24–162 h with valeric acid or 10%

NaOH added as appropriate to control the pH to pH 7.2–7.4. An average of 2.17 g Valeric acid was used/L/day and a total of 2.1 g NaOH was used.

(iii) Isobutyric acid added at an average rate of 3.71 g/L/day from 24–162 h with valeric acid or 10% NaOH added as appropriate to control the pH to pH 7.2–7.4. An average of 2.17 g Valeric acid was used/L/day and a total of 2.6 g NaOH was used.

(iv) Isobutyric acid added at an average rate of 4.38 g/L/day from 24–162 h with valeric acid or NaOH added as appropriate to control the pH to pH 7.2–7.4. An average of 3.13 g valeric acid was used/L/day and a total of 3.0 g NaOH was used.

The fermentations were harvested at 162 h unless otherwise stated and titres of the compound of formula (I) determined as follows:

| Acid | Compound of formula (I) mg/L | % Total Antibiotics S541 compounds |
|---|---|---|
| (i) H₂SO₄ = normal pH control | 460 | 46 |
| (ii) an average of 2.63 g/L/day isobutyric acid | 804 | 69 |
| (iii) an average of 3.71 g/L/day isobutyric acid | 714 | 58 |
| (iv) an average of 4.38 g/L/day isobutyric acid | 921 | 78 |

EXAMPLE 3

A liquid nitrogen strain of *Streptomyces cyaneogriseus noncyanogenus* NRRL 15773 was used to inoculate a 250 ml shake flask containing Medium A (50 ml) and incubated at 28° C. for 2 days on a rotary shaker operated at 250 rpm with a 2″ diameter orbital throw. 1 ml portions of this 2 day developed inoculum were used to inoculate further 250 ml shake flasks containing Medium A (50 ml) and incubated as previously described.

80 ml of the bulked shake flask developed inoculum was used to inoculate a fermenter (7 L) containing Medium C (4 L).

The fermentation was controlled to a temperature of 30° C. The culture was agitated et 500 rev/min and aerated at 3 L/min. The pH was controlled down to pH 7.4 by addition of 50/50 valeric acid/isobutyric acid from 18–162 h into the fermentation.

The fermentation was harvested at 162 h to give 250 mg/L of the compound of formula (I) corresponding to 84% total of the Antibiotics S541 compounds produced.

EXAMPLE 4

The inoculum stages of Example 1 using Medium A were followed. 80 ml of the bulked shake flask developed inoculum was used to inoculate a fermenter (7 L) containing Medium D (4 L).

| Medium D | gL⁻¹ |
|---|---|
| Glucose | 2.5 |
| Malt Dextrin MD 30E | 25.0 |
| Arkasoy 50 | 12.5 |
| Molasses | 1.5 |
| K₂HPO₄ | 0.125 |
| CaCO₃ | 1.25 |

Distilled water to 4 L, pH adjusted to 6.5 before autoclaving.

The fermentation was carried out for 24 h at a temperature of 28° C. with the culture agitated (500 rev/min) and aerated (3 L/min).

800 ml of this 24 h developed inoculum was used to inoculate a fermenter (70 L) containing Medium D (40 L). The fermentation was carried out for 24 h at a temperature of 28° C. with the culture agitated (550 rev/min) and aerated (30 L/min).

800 ml of this 24 h developed inoculum was used to inoculate Medium B (40 L) in a fermenter (70 L).

The fermentation was controlled to a temperature of 34° C. The culture was agitated (550 rev/min) and aerated (40 L/min) and 50/50 valeric acid/isobutyric acid was added at an average rate of 10 ml/h from 21 h to 117 h with 10% H₂SO₄ and 10% NaOH added as appropriate to control the pH to around pH 7.4.

The fermentation was harvested at 117 h to give 944 mg/L of the compound of formula (I) corresponding to 79% total of the Antibiotics S541 compounds produced.

EXAMPLE 5

The inoculum stages of Example 1 using Medium A were followed. 80 ml of the bulked shake flask developed inoculum was used to inoculate a fermenter (7 L) containing Medium D (4 L). The fermentation was carried out for 24 h at 28° C. with the culture agitated (500 rev/min) and aerated (4 L/min).

800 ml of this 24 h developed inoculum was used to inoculate a fermenter (70 L) containing Medium C (40 L).

The fermentation temperature was controlled to 34° C. The fermenter was agitated (550 rev/min) and aerated (40 L/min) and the pH controlled to around pH 7.3 by adding either (1) 80/20 valeric acid/isobutyric acid at an average rate of 6.67 g/L/day from 18 to 162 h or (2) 75/25 valeric acid/isobutyric acid added at an average rate of 6.34 g/L/day from 18 to 186 h.

The fermentations were harvested at 162 h and 186 h respectively to give either (1) 510 mg/L of the compound of formula (I) corresponding to 61% of the Antibiotics S541 compounds produced or (2) 516 mg/L of the compound of formula (I) corresponding to 72% total of the Antibiotics S541 compounds produced.

We claim:
1. A process for the production of a compound of formula (I)

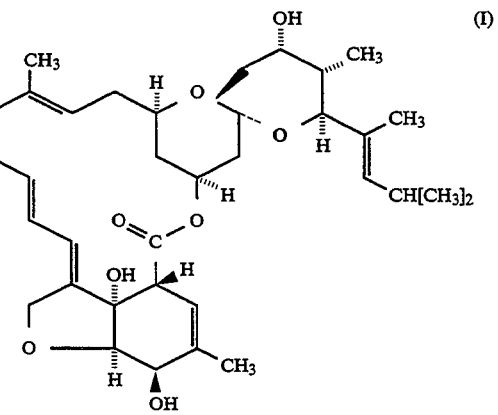

which comprises cultivating a microorganism selected from the group consisting of *Streptomyces thermoarchaensis* NCIB 12015, 12111, 12112, 12113, 12114 and mutants thereof capable of producing the compound of formula (I) in a culture medium containing an additive selected from the group consisting of a fatty acid, an ester of a fatty acid, an amide of a fatty acid and a salt of a fatty acid whereby the compound of formula (I) is produced; and then recovering the compound of formula I.

2. A process according to claim 1 in which the additive is isobutyric or valeric acid.

3. A process according to claim 1 in which the additive is a compound selected from the group consisting of isobutyric acid, valeric acid and salts thereof.

4. A process according to claim 1 wherein a fatty acid is added in an effective amount to said culture media to adjust the pH of said culture media to 5.5–7.5, and thereafter the pH is maintained in this range.

* * * * *